(12) United States Patent
Fujimoto et al.

(10) Patent No.: US 7,081,547 B2
(45) Date of Patent: Jul. 25, 2006

(54) PROCESS FOR PRODUCING FORMIC ESTER OR METHANOL AND SYNTHESIS CATALYST THEREFOR

(75) Inventors: Kaoru Fujimoto, Kitakyushu (JP); Noritatsu Tsubaki, Toyama (JP); Kenichiro Fujimoto, Futtsu (JP)

(73) Assignee: Nippon Steel Corporation, Tokyo (JP)

( * ) Notice: Subject to any disclaimer, the term of this patent is extended or adjusted under 35 U.S.C. 154(b) by 0 days.

(21) Appl. No.: 10/793,439

(22) Filed: Mar. 4, 2004

(65) Prior Publication Data

US 2004/0171704 A1   Sep. 2, 2004

Related U.S. Application Data

(62) Division of application No. 10/030,368, filed as application No. PCT/JP01/01386 on Feb. 23, 2001.

(30) Foreign Application Priority Data

Feb. 25, 2000  (JP) .............................. 2000-50046

(51) Int. Cl.
*C07C 67/36* (2006.01)
(52) U.S. Cl. .................................... 560/232
(58) Field of Classification Search ................ 560/232; 502/345
See application file for complete search history.

(56) References Cited

U.S. PATENT DOCUMENTS

| | | | |
|---|---|---|---|
| 4,876,286 A | 10/1989 | Sie et al. | |
| 4,888,361 A | 12/1989 | Sie et al. | |
| 4,939,292 A * | 7/1990 | Elliott et al. ................. | 560/239 |
| 4,994,603 A | 2/1991 | Mueller et al. | |
| 5,180,858 A | 1/1993 | Fleckenstein et al. | |
| 5,384,335 A | 1/1995 | Tierney et al. | |
| 5,401,873 A | 3/1995 | Zehner et al. | |

FOREIGN PATENT DOCUMENTS

| | | | |
|---|---|---|---|
| CA | 2304469 | | 4/1999 |
| DE | 863 046 | | 1/1953 |
| DE | 926 785 | | 4/1955 |
| EP | 309047 | | 3/1989 |
| JP | 57-88145 | | 6/1982 |
| JP | 3-151047 A | | 6/1991 |
| JP | 7-118187 | | 5/1995 |
| JP | 09-040610 | * | 2/1997 |
| JP | 9-40610 | | 2/1997 |
| JP | 10-195019 | * | 7/1998 |
| PL | 157499 | | 6/1992 |
| SU | 251569 | | 2/1970 |

OTHER PUBLICATIONS

Palekar et al., "Alkali compounds and copper chromite as low-temperature slurry phase methanol catalysts", Applied Catalysts A: General, 103:105-122 (1993).

Yingchun et al., "Phase transfer preparation of Cu-Mn catalyst for methyl formate synthesis directly from synthesis gas", Huaxue Yanjiu Yu Yingyong, 12:510-513 (2000) (Chemical Abstracts Service).

* cited by examiner

*Primary Examiner*—Paul A. Zucker
(74) *Attorney, Agent, or Firm*—Kenyon & Kenyon LLP

(57) ABSTRACT

A process for producing a formic ester comprises reacting carbon monoxide with an alcohol to produce a formic ester, wherein the reaction is performed in the presence of water and/or carbon dioxide and in the presence of (1) an alkali metal-type catalyst other than an alkali metal alkoxide and other than an alkali metal fluoride, or (2) an alkali metal-type catalyst other than an alkali metal alkoxide and other than an alkali fluoride in combination with an alkaline earth metal-type catalyst.

4 Claims, No Drawings

US 7,081,547 B2

PROCESS FOR PRODUCING FORMIC ESTER OR METHANOL AND SYNTHESIS CATALYST THEREFOR

This application is a divisional application under 35 U.S.C. §120 and 121 of prior Application No. 10/030,368 filed Oct. 25, 2001 which is a 35 U.S.C. §371 National Stage of International Application No. PCT/JP01/01386 filed Feb. 23, 2001, wherein International Application No. PCT/JP01/01386 was filed and published in the Japanese language. The entire disclosure of prior Application No. 10/030,368 is considered part of this divisional application and is hereby incorporated by reference.

TECHNICAL FIELD

The present invention relates to a process for producing a formic ester or methanol and a synthesis catalyst therefor. More specifically, the present invention relates to a process for producing a methanol from carbon monoxide and hydrogen using a catalyst having high resistance against decrease in the activity due to water or carbon dioxide and thereby obtaining a product with high efficiency, and also relates to a catalyst therefor.

BACKGROUND ART

Generally, in the industrial synthesis of a methanol, carbon monoxide and hydrogen (synthesis gas) obtained by steam reforming of a natural gas mainly comprising methane are used as the starting materials and the synthesis is performed using a copper/zinc-type catalyst or the like by a fixed-bed gas phase method under severe conditions of 200–300° C. and 5–25 MPa. Although this reaction is an exothermic reaction, efficient heat extraction can be hardly attained because of poor thermal conductivity in the gas phase method and a process of lowering the one-pass conversion and recycling unreacted high-pressure starting material gas is employed, which has, however, a severe problem in the efficiency. Despite such a problem, the fixed-bed gas phase method is not easily prone to the reaction inhibition by water or carbon dioxide contained in the synthesis gas and various plants are now operated by making use of this advantageous property.

On the other hand, various methods of synthesizing methanol in a liquid phase and thereby increasing the heat extraction rate are being studied. Among these, a method using a catalyst having high activity at low temperatures (approximately from 100 to 180° C.) is advantageous to the production system also in view of thermodynamics and being taken notice of. However, this method has been reported to suffer from quick decrease in the activity due to water and carbon dioxide contained in many cases in the synthesis gas and not used in practice.

DISCLOSURE OF INVENTION

The object of the present invention is to overcome the above-described problems and provide a catalyst and a method, where the catalyst activity is kept even when carbon dioxide, water and the like are included in the starting material gas and/or the reaction system at the synthesis of formic ester or methanol and the formic ester or methanol can be synthesized at low temperatures and low pressures.

The present invention is characterized by the followings.

(1) A process for producing a formic ester, comprising reacting carbon monoxide with an alcohol to produce a formic ester, wherein the reaction is performed in the presence of an alkali metal-type catalyst and/or an alkaline earth metal-type catalyst.

(2) A process for producing a methanol, comprising reacting carbon monoxide with an alcohol in the presence of an alkali metal-type catalyst and/or an alkaline earth metal-type catalyst to produce a formic ester, wherein a hydrogenolysis catalyst of formic ester and hydrogen are allowed to be present together in the reaction system to hydrogenate the produced formic ester and thereby obtain a methanol.

(3) A process for producing a methanol, comprising reacting carbon monoxide with an alcohol in the presence of an alkali metal-type catalyst and/or an alkaline earth metal-type catalyst to produce a formic ester, separating the produced formic ester and hydrogenating the separated formic ester by allowing a hydrogenolysis catalyst and hydrogen to be present together, thereby obtaining a methanol.

(4) A process for producing a methanol, comprising reacting an alcohol in the presence of an alkali metal-type catalyst and/or an alkaline earth metal-type catalyst, and a catalyst that includes Cu simultaneously with Mn and/or Re to obtain a methanol from carbon monoxide and hydrogen.

(5) A process for producing a formic ester, comprising reacting carbon monoxide with an alcohol, wherein the reaction is performed in the presence of a catalyst containing Cu simultaneously with Mn and/or Re.

(6) The production process as described in any one of (1) to (4), wherein the alkali metal-type catalyst and the alkaline earth metal-type catalyst include an alkali metal salt and a catalyst containing an alkaline earth metal salt, respectively.

(7) The process for producing a methanol as described in (2) or (3), wherein the hydrogenolysis catalyst is a solid and the alkali metal-type catalyst and/or the alkaline earth metal-type catalyst is supported on this solid catalyst and used for the reaction.

(8) The production process as described in any one of (1) to (5), wherein the alcohol is a primary alcohol.

(9) A catalyst for producing a methanol, which is obtained by loading an alkali metal-type catalyst and/or an alkaline earth metal-type catalyst on a solid hydrogenolysis catalyst for formic ester.

(10) A catalyst for producing a methanol, which is composed of an alkali metal-type catalyst and/or an alkaline earth metal-type catalyst, as well as a catalyst containing Cu simultaneously with Mn and/or Re.

(11) A catalyst for producing a formic ester, comprising Cu simultaneously with Mn and/or Re.

The present invention is described in detail below.

As a result of extensive investigations, the inventors of the present invention have found that when an alkali metal-type catalyst and/or an alkaline earth metal-type catalyst substantially free from poisoning with water and/or carbon dioxide is used, a formic ester can be produced from a carbon monoxide and an alcohol even if water and/or carbon dioxide co-exist. The present invention has been accomplished based on this finding. Examples of alkali metal-type catalysts include metal compounds and elementary substances, such as lithium, potassium, sodium and cesium. Examples of the alkaline earth metal-type catalysts include metal compounds and elementary substances, such as calcium, magnesium, barium and strontium. The metal compounds are preferably metal salts or metal oxides, more preferably alkali metal salts such as carbonates, nitrates, phosphates, acetates and formates. Here, alkali metal alkoxides (e.g., methoxide, ethoxide) are excluded because these are substantially subjected to poisoning with water and/or carbon dioxide. Those catalysts can also be used as a catalyst supported on a general support by an ordinary method. The alcohols used for the reaction are an alcohol resultant from bonding of a hydroxyl group to a chained or alicyclic hydrocarbon and in addition, may be a phenol or a substitution product thereof, or a thiol or a substitution product thereof. These alcohols may be primary, secondary or tertiary alcohols, but preferably primary alcohols due to their reaction efficiency. Lower alcohols, such as methyl alcohol or ethyl alcohol, are most commonly used. The reaction may be performed in either the liquid or gas phase but a system where moderate conditions can be selected may be employed. To speak specifically, the temperature, the pressure and the reaction time are selected from 70 to 250° C., 3 to 70 atm and 5 minutes to 10 hours, respectively, however, the conditions are not limited thereto. The alcohol may be sufficient if the amount added thereof is sufficiently large to allow the reaction to proceed, however, the alcohol may also be used as a solvent and in an amount larger than that. In this reaction, organic solvents other than alcohols may be appropriately used in combination.

A catalyst containing Cu simultaneously with Mn and/or Re may also be used in the production of a formic ester.

The obtained formic ester may be purified by an ordinary method but may also be used as it is in the production of a methanol. That is, a methanol can be produced by hydrogenating the formic ester. For the hydrogenolysis, a hydrogenolysis catalyst is used and examples of the catalyst which can be used include general hydrogenolysis catalysts containing Cu, Pt, Ni, Co, Ru or Pd. More specifically, copper-type catalysts such as $Cu/MnO_x$, $Cu/ReO_x$ (wherein X is a chemically allowable value), $Cu/ZnO$, $Cu/CrO_3$ and Raney copper, and nickel-type catalysts are suitably used. Among these, $Cu/MnO_x$ and $Cu/ReO_x$ exhibit extremely high activities in this reaction and ensure a high methanol yield even when water and/or carbon dioxide are present. The method for preparing the hydrogenolysis catalysts is not particularly limited and an ordinary method may be used, such as impregnation method, precipitation method, sol-gel method, coprecipitation method, ion exchange method, kneading method and drying method. However, according to the coprecipitation method, a catalyst having a high loading amount can be prepared and good results can be readily obtained. In the present invention, this hydrogenolysis catalyst and hydrogen are allowed to be present together in the reaction system for producing a formic ester from a carbon monoxide and an alcohol, whereby a methanol can be produced by a so-called one-step process. The hydrogenolysis reaction can be performed fundamentally under the above-described reaction conditions, however, the temperature and the pressure may be appropriately changed. The hydrogen/carbon monoxide ratio is generally selected in the range approximately from 1 to 5. As described above, in the case of performing the reaction while allowing a hydrogenolysis catalyst to be present together with an alkali metal-type catalyst and the like, these catalysts may be used as a simple mixture, however, when the alkali metal-type catalyst is supported on the solid hydrogenolysis catalyst, the recovery of the catalysts is advantageously facilitated. With respect to the loading method itself, an ordinary method employed in the preparation of catalysts may be used.

In the case where a methanol can hardly be produced by the one-step process, it is also possible to obtain a methanol by separating the produced formic ester and then hydrogenolyzing the separated formic ester in the presence of a hydrogenolysis catalyst and hydrogen.

The process for producing a formic ester or a methanol according to the present invention is presumed to proceed according to the following reaction scheme (as an example, a case of using an alcohol resulting from bonding a hydroxyl group to a chained or alicyclic hydrocarbon is shown):

$$R-OH + CO \rightarrow HCOOR \quad (1)$$

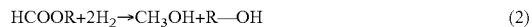

$$HCOOR + 2H_2 \rightarrow CH_3OH + R-OH \quad (2)$$

(wherein R represents an alkyl group).

As such, carbon monoxide and hydrogen are used as the starting materials for producing a methanol and the alcohol can be recovered and reused. According to the present invention, even where a fairly large amount of water and carbon dioxide are present in the starting material gas (for example, even with at least 5% of carbon dioxide) and/or the reaction system, the catalyst does not lose its activity and a formic ester or a methanol can be produced. Furthermore, even where a sulfur-type compound and a chlorine-type compound, such as $H_2S$ and $HCl$, are mingled in the reaction system, the formic ester or a methanol can be similarly produced without any problem.

BEST MODE FOR CARRYING OUT THE INVENTION

The present invention is described in greater detail by referring to the Examples given below, although the present invention is not limited to these Examples.

In the Examples, the CO conversion and the methanol yield were calculated according to the following formulae:

CO conversion (%)=[1−(molar number of $CO+CO_2$ recovered after reaction)/(molar number of $CO+CO_2$ charged)]×100

Methanol yield (%)=((molar number of methanol produced)/(molar number of $CO+CO_2$ charged))×100

EXAMPLE 1

In an autoclave having a content volume of 80 ml, 0.72 mmol of potassium carbonate was added to 10 ml of ethanol containing 1% by mass of water as a solvent, a carbon dioxide mixed synthesis gas (CO: 32%, $CO_2$: 4.7%, balance: hydrogen) was filled to 3 MPa, and the reaction was performed at 170° C. for 2 hours. The reaction product was analyzed by gas chromatograph, as a result, it was found that only ethyl formate was obtained with a CO conversion of 3.0%.

EXAMPLE 2

The reaction was performed by the method described in Example 1 except for changing the reaction time to 20 minutes. The same results as in Example 1 were obtained and it was revealed that the reaction reached the equilibrium in 20 minutes.

EXAMPLE 3

The reaction was performed by the method described in Example 1 except for adding potassium hydrogencarbonate in place of potassium carbonate. As a result, ethyl formate was obtained with a CO conversion of 3.1%.

EXAMPLE 4

The reaction was performed by the method described in Example 1 except for adding cesium carbonate in place of potassium carbonate. The CO conversion was 3.2%.

EXAMPLE 5

The reaction was performed by the method described in Example 1 except for adding sodium carbonate in place of potassium carbonate. The CO conversion was 1.36%.

EXAMPLE 6

The reaction was performed by the method described in Example 1 except for adding lithium carbonate in place of potassium carbonate. The CO conversion was 0.4%.

EXAMPLE 7

The reaction was performed by the method described in Example 1 except for adding potassium nitrate in place of potassium carbonate. The CO conversion was 1.0%.

EXAMPLE 8

The reaction was performed by the method described in Example 1 except for adding sodium nitrate in place of potassium carbonate. The CO conversion was 0.9%.

EXAMPLE 9

The reaction was performed by the method described in Example 1 except for adding potassium phosphate in place of potassium carbonate. The CO conversion was 1.7%.

EXAMPLE 10

The reaction was performed by the method described in Example 1 except for adding potassium acetate in place of potassium carbonate. The CO conversion was 1.51%.

EXAMPLE 11

The reaction was performed by the method described in Example 1 except for adding potassium formate in place of potassium carbonate. The CO conversion was 3.44%.

EXAMPLE 12

The reaction was performed by the method described in Example 1 except for using methanol in place of ethanol, as a result, the CO conversion was 4.0% (methyl formate).

EXAMPLE 13

The reaction was performed by the method described in Example 1 except for using n-propanol in place of ethanol. The CO conversion was 3.4% (n-propyl formate).

EXAMPLE 14

The reaction was performed by the method described in Example 1 except for using n-butanol in place of ethanol. The CO conversion was 3.4% (n-butyl formate).

EXAMPLE 15

The reaction was performed by the method described in Example 1 except for using i-propanol in place of ethanol. The CO conversion was 1.1% (i-propyl formate).

EXAMPLE 16

The reaction was performed by the method described in Example 1 except for using i-butanol in place of ethanol. The CO conversion was 1.8% (i-butyl formate).

EXAMPLE 17

The reaction was performed by the method described in Example 1 except for using t-butanol in place of ethanol. The CO conversion was 0.7% (t-butyl formate).

EXAMPLE 18

The reaction was performed by the method described in Example 1 except for further adding 0.2 g of a copper/zinc coprecipitated catalyst as the hydrogenolysis catalyst. As a result, methanol was obtained with the CO conversion of 2.9% and the methanol yield of 0.3%.

EXAMPLE 19

In an autoclave having a content volume of 85 ml, 1.4 mmol of potassium carbonate was added to 20 ml of ethanol containing 0.010% by mass of water as a solvent, a carbon dioxide mixed synthesis gas (CO: 32%, $CO_2$: 4.7%, balance: hydrogen) was filled to 3.0 MPa, and the reaction was performed at 170° C. for 2 hours. The reaction product was analyzed by gas chromatograph. As a result, it was found that only ethyl formate was obtained with the CO conversion of 16%.

EXAMPLE 20

The reaction was performed by the method described in Example 19 except for further adding 4.0 g of a copper/zinc coprecipitated catalyst as the hydrogenolysis catalyst. As a result, methanol was obtained with the CO conversion of 25% and the methanol yield of 1.2%.

EXAMPLE 21

The reaction was performed by the method described in Example 19 except for further adding 4.0 g of a copper/manganese coprecipitated catalyst as the hydrogenolysis catalyst. As a result, methanol was obtained with the CO conversion of 90% and the methanol yield of 27%.

EXAMPLE 22

The reaction was performed by the method described in Example 19 except for further adding 2.0 g of a copper/manganese coprecipitated catalyst as the hydrogenolysis catalyst. As a result, methanol was obtained with the CO conversion of 79% and the methanol yield of 27%.

EXAMPLE 23

The reaction was performed by the method described in Example 19 except for further adding 1.0 g of a copper/manganese coprecipitated catalyst as the hydrogenolysis catalyst. As a result, methanol was obtained with the CO conversion of 33% and the methanol yield of 1.1%.

EXAMPLE 24

The reaction was performed by the method described in Example 22 except that the mixed synthesis gas did not contain $CO_2$. As a result, methanol was obtained with the CO conversion of 92% and the methanol yield of 41%.

The invention claimed is:

1. A process for producing a formic ester, comprising reacting carbon monoxide with an alcohol to produce a formic ester, wherein the reaction is performed in the presence of water and/or carbon dioxide and in the presence of (1) an alkali metal-type catalyst other than an alkali metal alkoxide and other than an alkali fluoride, or (2) an alkali metal-type catalyst other than an alkali metal alkoxide and other than an alkali fluoride in combination with an alkaline earth metal-type catalyst.

2. The production process as claimed in claim 1, wherein the alcohol is a primary alcohol.

3. The production process as claimed in claim 1, wherein the alkali metal-type catalyst other than an alkali metal metal alkoxide and other than an alkali fluoride is a catalyst containing an alkali metal salt.

4. The production process as claimed in claim 3, wherein the alkaline earth metal-type catalyst is a catalyst containing an alkaline earth metal salt.

* * * * *